(12) United States Patent
Kanbara

(10) Patent No.: US 6,712,800 B2
(45) Date of Patent: Mar. 30, 2004

(54) BODY WASTE COLLECTOR

(75) Inventor: Noriyuki Kanbara, Soka (JP)

(73) Assignee: Alcare Co., Ltd., Tokyo (JP)

( * ) Notice: Subject to any disclaimer, the term of this patent is extended or adjusted under 35 U.S.C. 154(b) by 90 days.

(21) Appl. No.: 10/192,398

(22) Filed: Jul. 10, 2002

(65) Prior Publication Data

US 2003/0014023 A1 Jan. 16, 2003

(30) Foreign Application Priority Data

Jul. 10, 2001 (JP) ........................................ 2001-208748

(51) Int. Cl.⁷ .................................................. A61F 5/44
(52) U.S. Cl. ...................................... 604/333; 604/337
(58) Field of Search ................................. 604/327–345

(56) References Cited

U.S. PATENT DOCUMENTS

| | | | |
|---|---|---|---|
| 4,411,659 A | 10/1983 | Jensen et al. ............... | 604/332 |
| 5,074,851 A | 12/1991 | Plass et al. ................. | 604/333 |
| 5,250,042 A | 10/1993 | Torgalkar et al. ........... | 604/333 |
| 5,306,264 A | 4/1994 | Ferguson et al. ............ | 604/333 |
| 5,690,623 A | * 11/1997 | Lenz et al. .................. | 604/333 |

* cited by examiner

Primary Examiner—Weilun Lo
Assistant Examiner—Linh Truong
(74) Attorney, Agent, or Firm—Haverstock, Garrett & Roberts LLP

(57) ABSTRACT

The present invention provides a body waste collector which allows the discharge of the gases in the ostomy bag over a long time and is, in addition, highly economical. The body waste collector comprises an ostomy bag 2 formed by sealing together the peripheral edge portions 16 of two films 7, 8 for collecting the body wastes, a faceplate 1 coupled to one film 7 of the ostomy bag, a gas-discharging vent 11 provided in the other film 8 of the ostomy bag so as to connect the inside of the ostomy bag to the outside thereof, and a deodorizing filter 12 disposed so as to communicate with the gas-discharging vent 11, wherein, between the two films 7, 8 of the ostomy bag, there is disposed an intermediate wall 13 which is comprised of a fluid-impermeable material and divides the space 10 in the ostomy bag into two regions, i.e., the region 20 at the faceplate side and the region 21 at the deodorizing filter side; this intermediate wall is disposed so as to face the whole surfaces of both the opening 6 in the faceplate and the deodorizing filter 12, and further, in the peripheral portion of the intermediate wall 13, there are formed a plurality of fluid inlets 24, 25 which connect the region 20 at the faceplate side and the region 21 at the deodorizing filter side.

9 Claims, 4 Drawing Sheets

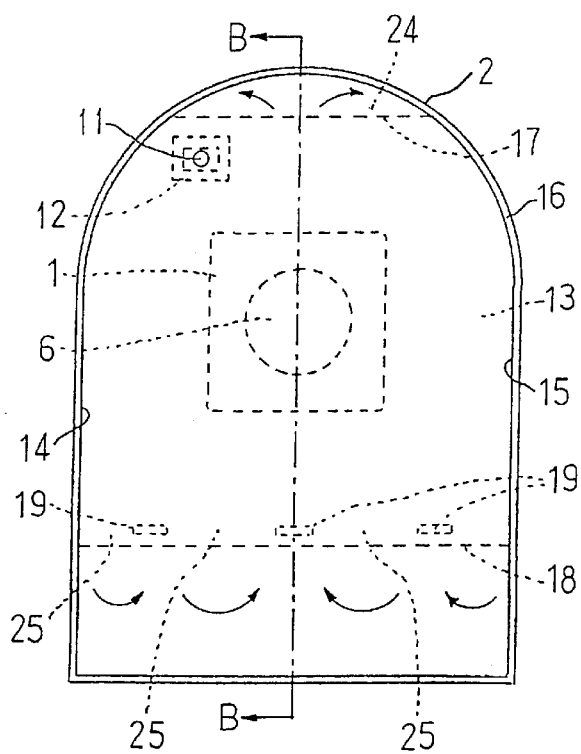
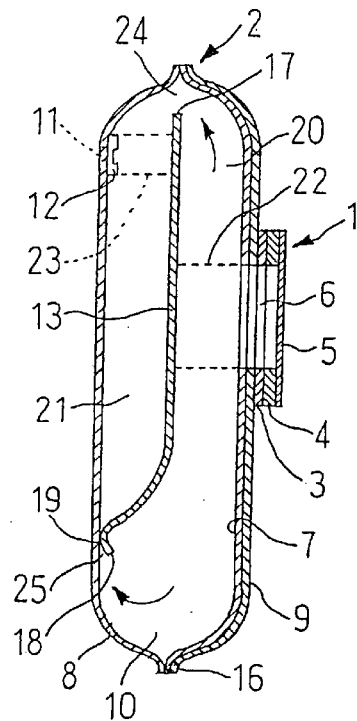
Fig. 1A    Fig. 1B
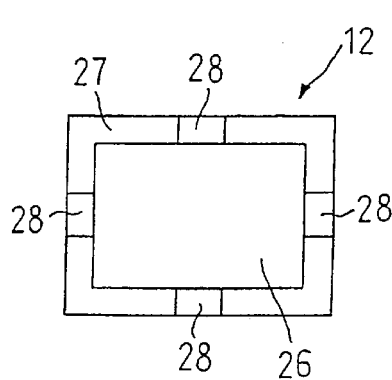
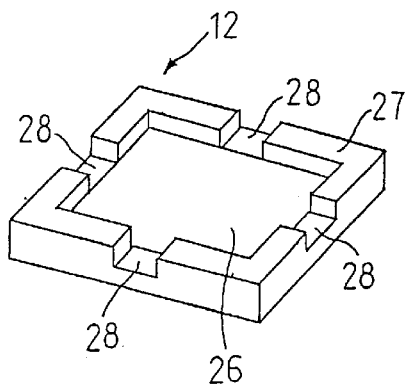
Fig. 2A    Fig. 2B

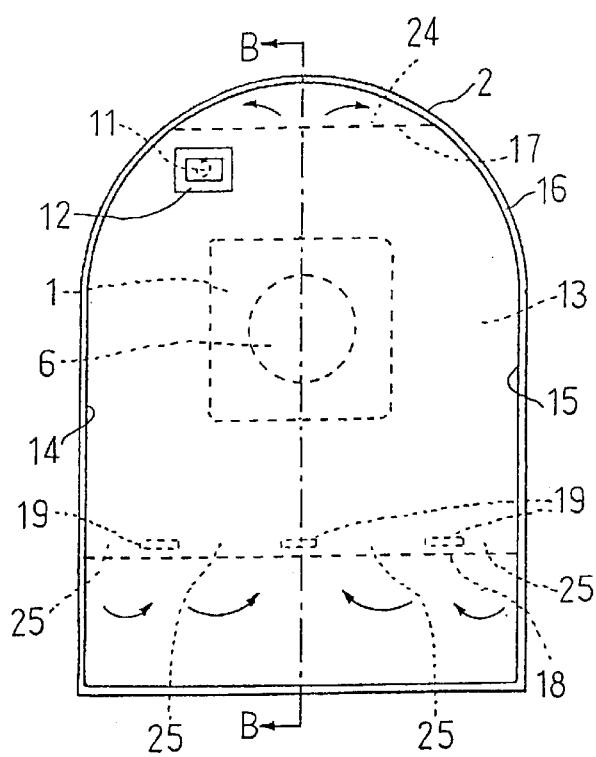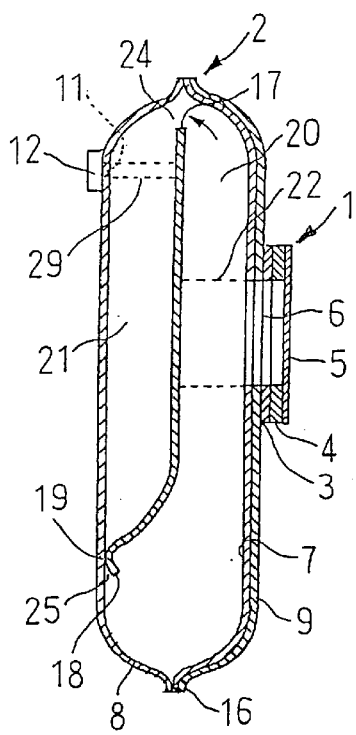
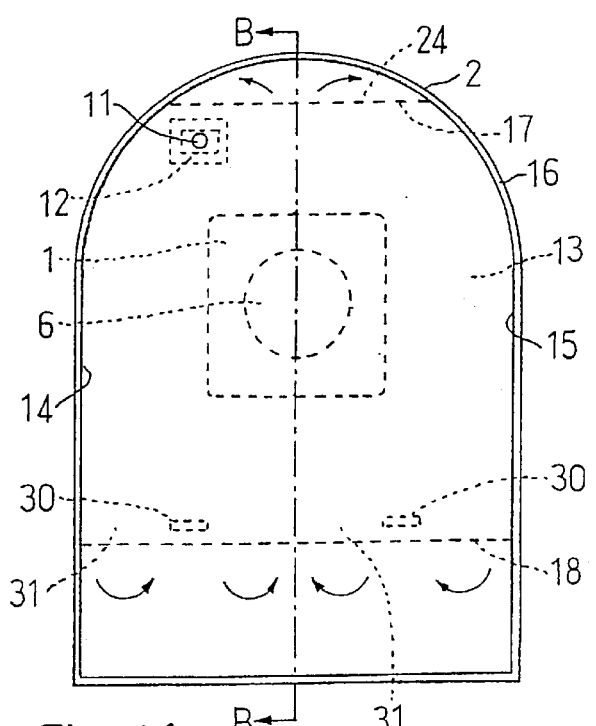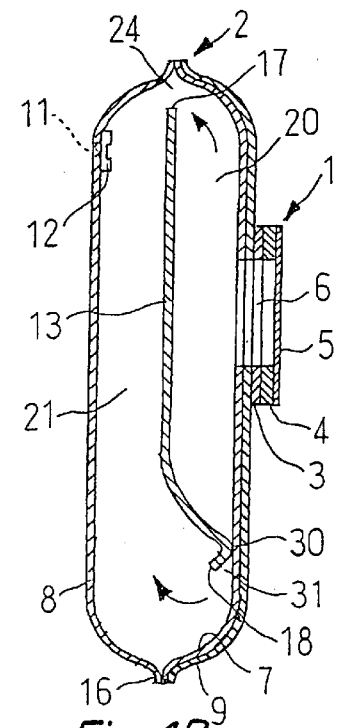

BODY WASTE COLLECTOR

Applicant hereby claims foreign priority benefits under 35 U.S.C. §119 of corresponding Japanese patent application No. 2001-208748, filed Jul. 10, 2001.

The present invention relates to a body waste collector equipped with a mechanism that is fitted onto a stoma formed in a human body so as to temporarily store therein the solid body wastes and liquid body wastes, etc. (hereinafter referred to merely as body wastes) excreted from the stoma and discharge the gases produced from the stoma in the human body and from the body wastes, from within an ostomy bag to the outside of the ostomy bag.

BACKGROUND OF THE INVENTION

A body waste collector is used for disposing of the body wastes excreted from the stoma formed in the surface of a patient after the surgical operation of the patient; such a body waste collector is generally comprised of an ostomy bag and a faceplate that is mountable onto the stoma in the surface of a human body. The faceplate is adherently fixed to the portion around the stoma in the body surface by means of a adhesive layer and has the function of guiding the body wastes into the ostomy bag and at the same time holding the ostomy bag. The body wastes are accompanied with odorous gases in some cases, and, as the body wastes are excreted, the gases also collect in the ostomy bag, so that, unless the gases are suitably vented, there is the danger that the ostomy bag may finally come to a rupture; if the ostomy bag bursts, a large amount of body wastes leak out. In order to avoid the occurrence of such a state, it is practiced that a deodorizing filter is provided on a portion of the ostomy bag, so that the gases discharged into the ostomy bag are dissipated out from within the ostomy bag, removing the odors by passing the gases through the deodorizing filter. However, if this deodorizing filter is directly exposed to the body wastes, then the body wastes stick to the surface of the filter, as a result of which there arises the danger that the filter may be clogged to lower the gas permeability thereof, so that the ostomy bag may be expanded and finally come to a rupture and/or the ostomy bag may peel off from the human body, and further, there is the problematic point that the body wastes penetrate into the deodorizing filter to leak outside.

In order to give solutions to these problems, a number of methods for avoiding the attachment of the body wastes to the filter have so far been proposed. One method is to cover the surface of the deodorizing filter or a portion or the whole of the gas-discharge path leading to the deodorizing filter, by the use of a cover layer formed of a gas-permeable and liquid-impermeable or hardly liquid-permeable material, whereby the gases penetrate through the cover layer and reach the deodorizing filter, but the body wastes, particularly the liquid body wastes, are blocked by the cover layer and thus prevented from penetrating into the deodorizing filter (See, e.g., U.S. Pat. Nos. 5,074,851 and 5,250,042). However, since the body wastes are slurry-like and viscous, there arises the problem that, even if the surface of the filter is covered with, e.g., a liquid-impermeable cover layer, the minute particles in the body wastes stick to the surface of the cover layer and, further, form a film on the surface of the cover layer, as a result of which the gases become unable to pass through the cover layer.

In order to give a solution to the above-mentioned problem, there has been proposed a multi-stage filter system constituted such that there is provided a multi-stage filter comprising a deodorizing filter, a microporous protection film for protecting the deodorizing filter from the liquid, an open-cell foam barrier for protecting the microporous protection film from the semi-solid fluid and the liquid, and a fluid-impermeable plastics film cover with a gas path, whereby the contact of the body wastes with the deodorizing filter can be avoided as much as possible (See U.S. Pat. No. 5,306,264). This system is advantageous in respect of the time spent until the body wastes reach the deodorizing filter, but it cannot be prevented that the part of the multi-stage filter in which the gases flow in is clogged with the body wastes, so that the gas venting ability of the filter as a whole lowers. As stated above, even if the filter itself is improved as mentioned above, it is difficult, due to the characteristics of the body wastes, to prevent the gas venting ability from falling so long as there is employed such a structure that there is the possibility that the body wastes may be contacted with the filter portion.

There is further proposed a structure constituted such that, as a different means, an intermediate barrier wall comprised of a thermoplastic film is disposed between the stoma in the human body and a gas discharge port in the internal space of an ostomy bag, a communication hole is provided in the upper part of this intermediate barrier wall so that the gases from the opening may reach the deodorizing filter only through the communication hole in the intermediate barrier wall, and the filter is not directly exposed to the body wastes discharged from the stoma, wherein a selected surface of the walls is embossed so that the intermediate barrier wall and the two walls forming the ostomy bag may not closely attach together and obstruct the flow of gases through the interior of the ostomy bag (See U.S. Pat. No. 4,411,659). By this structure, a marked improvement is made in respect of the prevention of the filter itself from becoming filthy, but, in this case, there arises the problem that, if the communication aperture is made dirty by the body wastes, then the appropriate gas flow in the ostomy bag is obstructed, and further, the communication aperture is blocked by the body wastes, whereby the intermediate barrier wall comes to closely attach to the surface of the filter and/or the ostomy bag walls in the ostomy bag.

OBJECT OF THE INVENTION

It is the object of the present invention to provide a body waste collector that can continuously maintain the discharge of gases in the ostomy bag for a long time and, in addition, economically excellent.

SUMMARY OF THE INVENTION

In order to solve the above-mentioned problems, the body waste collector according to the present invention comprises an ostomy bag formed by sealing together the peripheral edge portions of two films in order to receive the body wastes discharged from a stoma formed in a human body, a faceplate which is coupled to one of the films constituting the ostomy bag and is to be set onto the stoma of the human body, a gas-discharging vent provided in the other film of the ostomy bag so as to connect the inside of the ostomy bag to the outside thereof, and a deodorizing filter disposed in the ostomy bag so as to communicate with the gas-discharging vent, wherein, between the two films constituting the ostomy bag, there is disposed an intermediate wall consisting of a fluid-impermeable material, said intermediate wall dividing the space in the ostomy bag into two regions, i.e., the region at the faceplate side and the region at the deodorizing filter side, said intermediate wall being disposed in such manner as to face horizontally the whole surfaces of both the opening in the faceplate and the deodorizing filter in the state in which the body waste collector is supported vertically, and, in the peripheral portion of the intermediate wall, there are formed a plurality of fluid inlets which connect the region at the faceplate side to the region at the deodorizing filter.

Further, according to the present invention, the body waste collector comprises an ostomy bag formed by sealing together the peripheral edge portions of two films in order to receive the body wastes discharged from a stoma formed in a human body, a faceplate which is coupled to one of the films constituting the ostomy bag and is to be set onto the stoma of the human body, a gas-discharging vent provided in the other film of the ostomy bag so as to connect the inside of the ostomy bag to the outside thereof, and a deodorizing filter disposed on the outer side of the ostomy bag so as to communicate with the gas-discharging vent, wherein, between the two films constituting the ostomy bag, there is disposed an intermediate wall consisting of a fluid-impermeable material, said intermediate wall dividing the space in the ostomy bag into two regions, i.e., the region at the faceplate side and the region at the gas-discharging vent side, said intermediate wall being disposed in such a manner as to face horizontally the whole surfaces of both the opening in the faceplate and the gas-discharging vent in the state in which the body waste collector is supported vertically, and, in the peripheral portion of the intermediate wall, there are formed a plurality of fluid inlets which connect the region at the faceplate side to the region at the gas-discharging vent side.

BRIEF DESCRIPTION OF THE DRAWINGS

FIG. 1A is a front view showing an embodiment of the present invention, and FIG. 1B is a longitudinal sectional view taken along the line B—B in FIG. 1A.

FIG. 2A is an enlarged front view showing an embodiment of the deodorizing filter according to the present invention, and FIG. 2B is an enlarged perspective view of the embodiment of the deodorizing filter according to the present invention.

FIG. 3A is a front view of a different embodiment of the present invention, and FIG. 3B is a longitudinal sectional view taken along the line B—B in FIG. 3A.

FIG. 4A is a front view of a different embodiment of the invention, and FIG. 4B is a longitudinal sectional view taken along the line B—B in FIG. 4A.

DETAILED DESCRIPTION OF THE PREFERRED EMBODIMENTS

Figure 5A:
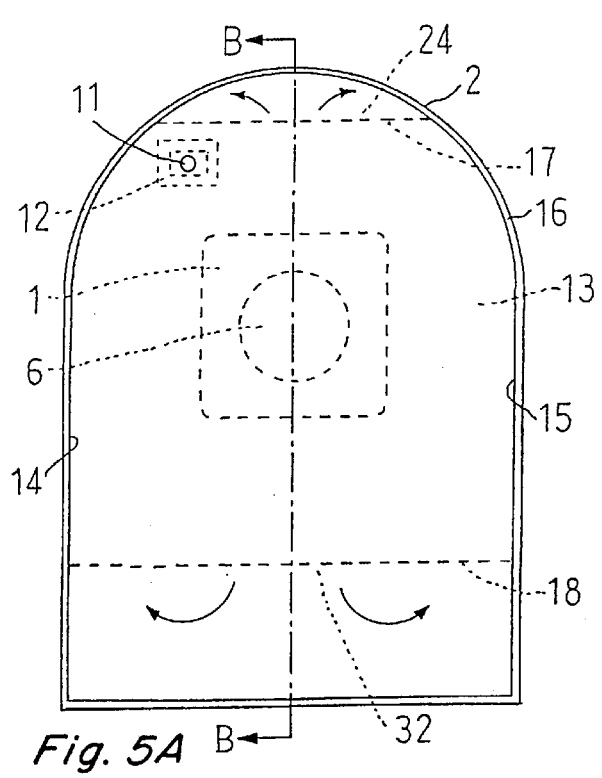
FIG. 5A is a front view of still different an embodiment of the invention.

Referring to FIGS. 1A and 1B, the reference numeral 1 denotes a faceplate for holding the body waste collector on a stoma portion formed in the surface of a human body, and numeral 2 denotes an ostomy bag that is coupled to the faceplate and is to collect the body wastes therein. The faceplate 1 comprises a flange layer 3, an adhesive layer 4 and a release film 5, which are formed as one integral body with the adhesive layer 4 set at the human body side, that is, the skin-contacting side; and the faceplate 1 has an opening 6 in the center. The ostomy bag 2 is fixed onto the flange layer 3 at the non-skin-contacting side and can receive the body wastes discharged through the opening 6 in the faceplate 1 from the stoma in the human body to which the faceplate 1 is fixed by means of the adhesive layer 4. The ostomy bag 2 comprises an inner side (human body side) film 7 and an outer side (the opposite side with respect to the human body) film 8, and, at the skin side of the inner side film 7, there is disposed a non-woven fabric 9 for preventing the occurrence of a sticky feeling and a sweaty state due to the contact between the skin and the inner side film 7, the inner side film 7, the outer side film 8 and the non-woven fabric 9 are sealed together in the peripheral potion thereof by means of e.g., heat sealing, whereby an internal space 10 is formed. Numeral 11 denotes a gas-discharging vent in the upper portion of the outer side film 8 so as to connect the inside of the ostomy bag to the outside thereof. The shape of the gas-discharging vent 11 may be arbitrarily determined; the gas-discharging vent can be provided in the form of one or more U-shaped, V-shaped, linear or other-shaped slits or circular, oval or otherwise shaped holes. Numeral 12 denotes a deodorizing filter mounted on the inner side of the outer side film 8 of the ostomy bag so as to cover the gas-discharging vent 11. The deodorizing filter 12 is desirably disposed in such a manner that, in the state in which the body waste collector is normally used, the deodorizing filter 12 is located at a position higher than the opening 6 of the faceplate 1 and shifted laterally with respect to the opening in the faceplate and in such a manner that the linear distance between the deodorizing filter and the opening in the faceplate becomes as large as possible.

Numeral 13 denotes is an intermediate wall formed of a film composed of a fluid-impermeable material, and sides 14 and 15 of the film 13 are fixed, over the whole length thereof, to the outer peripheral edges 16 of the films 7 and 8 of the ostomy bag by heat sealing, and further, an upper side 17 of the intermediate wall 13 is a free end that is not fixed, while a lower side 18 thereof is partially fixed at positions 19 (three positions in the embodiment shown) to the outer side film 8 by partially welding. This intermediate wall 13 divides the internal space 10 of the ostomy bag into a region 20 at the faceplate 1 side and a region 21 at the deodorizing filter 12 side and has at least such a size that, in the state in which the faceplate 1 and the ostomy bag 2 are supported vertically, the intermediate wall 13 can face, in the horizontal direction, at least the whole surfaces of both the opening 6 in the faceplate 1 and the deodorizing filter 12. In other words, the size of the intermediate wall 13 must be such that, as shown in FIG. 1A, broken lines 22 drawn horizontally from the outermost periphery of the opening 6 in the faceplate 1 and broken lines 23 drawn horizontally form the outermost periphery of the deodorizing filter 12 can be accommodated within the surface of the intermediate wall 13. Further, above the upper side 17 of the intermediate wall 13, there is formed a fluid inlet 24 that connects the region 20 at the faceplate side to the region 21 at the deodorizing filter side, while, in the lower portion of the intermediate wall 13, there are formed fluid inlets 25 that connect the region 20 at the faceplate side to the region 21 at the deodorizing filter side between partially welding portions 19; these fluid inlets 25 serve as fluid flow paths extending from the region 20 at the faceplate side to the region 21 at the deodorizing filter side as indicated by arrows.

As for the materials constituting the faceplate 1 and the ostomy bag 2, there can be used materials similar to the materials conventionally used. For the flange layer 3 of the faceplate, materials such as polyethylene, ethylene-vinyl acetate copolymer, ethylene-ethyl acrylate copolymer, ethylene-methyl acrylate copolymer, polypropylene, polyvinyl chloride, polyester, polyamide, etc. can be used either singly or in combination. For the adhesive layer 4, there can be used a skin protecting agent consisting of a hydrophilic polymer and a hydrophobic polymer. For both films 7, 8 and the intermediate wall 13 of the ostomy bag 2, there can be used single-component films consisting of materials such as polyvinylidene chloride, polyethylene, polyvinyl chloride, and chlorinated polyethylene, or materials prepared by blending or copolymerizing these components with vinyl acetate, polyacrylic acid, or composite films of above mentioned materials etc. For the non-woven fabric 9, there can be used, for example, a polypropylene/polyethylene conjugate non-woven fabric.

For the material of the deodorizing filter 12, there can also be used a material similar to the material conventionally used. FIGS. 2A and 2B show an embodiment of the deodorizing filter 12, wherein numeral 26 denotes the deodorizing element, which is constituted such that a gas-permeable, water-proof film (such as, e.g., polyamide/modified acrylic polymer non-woven fabric) and a deodorant (such as, e.g., granular activated charcoal, fibrous activated charcoal or the like) are stuck together with a reticulate hot-melt adhesive, and, to the surface at that side of the deodorant which is opposite to the gas-permeable, water-proof film, a porous sheet (such as, e.g., a porous laminate sheet) is stuck; and the thus formed deodorizing element is accommodated in a rectangular parallelepiped housing 27. The housing 27 is constituted such that, in the surface thereof at the incorporated gas-permeable, water-proof film side, a plurality of grooves 28 (four, in the embodiment shown) are provided. The housing 27 is mounted on the inner surface of the outer film 8 of the ostomy bag in such a manner that the groove 28 side of the filter 12 faces the intermediate wall 13 to allow communication with the gas discharging vent 11. By providing the grooves 28 in this manner, it is ensured that, even if the film constituting the intermediate wall 13 attaches to the surface of the housing 27, the gas inlets are secured through the grooves 28, and thus, the gases can flow into the deodorizing filter 12. By setting the thickness of the housing 27 to 1 mm or more, it is ensured that a space is formed between the film 8 of the ostomy bag and the intermediate wall 13 to prevent the close contact between the film 8 of the ostomy bag and the intermediate walls 13, and thus, a suitable gas flow paths are formed in the vicinity of the deodorizing filter. The shape of the housing of the deodorizing filter is not limited to a rectangular shape, but a circular shape or any other arbitrary shape can be used. Further, by roughening that surface of the housing 27 which faces the intermediate wall, it becomes possible to prevent the intermediate wall 13 to closely attach to the surface of the housing 27 even in case the film constituting the intermediate wall 13 covers the housing 27, and further, gas inlets are secured through the clearances formed between the intermediate wall 13 and the rugged surface of the housing 27 as in the case of the effect produced by the above-mentioned grooves 28, so that a good gas venting can be maintained.

The body waste collector shown in FIGS. 1A and 1B is used as follows: When it is set onto a human body, the release film 5 of the faceplate 1 is removed, and then, the faceplate 1 is attached to the surface of the human body by means of the adhesive layer 4 in such a state that the stoma formed in the human body is aligned with the opening 6 in the faceplate 1. The body wastes discharged from the stoma in the human body are passed through the opening 6 of the faceplate 1 into the region 20 at the faceplate side of the internal space 10 of the ostomy bag 2 and then falls to the bottom of the ostomy bag 2, but, since the intermediate wall 13 is comprised of a fluid-impermeable material, it never happens that the body wastes should penetrate through the intermediate wall 13 into the region 21 at the deodorizing filter side. The gases and odors produced from the body wastes pass through the respective fluid inlets 24 and 25 formed above and in the lower portion of the intermediate wall 13, entering the region 21 at the deodorizing filter side, where odors are adsorbed or changed into odorless substances by the deodorant in the deodorizing filter 12 and the gases which are thus made odorless are discharged outside via the gas discharging vent 11. In this case, since the fluid inlets 24 and 25 exist above and in the lower portion of the intermediate wall 13, the gases are subjected to only a very low resistance, and the majority of the body wastes is blocked by the intermediate wall 13 and thus fall into the region 20 at the faceplate side; even if some of the body wastes sticks to the upper fluid inlet 24, it is let down by the flow of gases; and further, even if some of the body wastes sticks to the fluid inlets 25 in the lower portion of the intermediate wall, it is similarly let down by the flow of the gases. There is thus only a very slight possibility that some of the body wastes may stick to the surface of the deodorizing filter 12.

FIGS. 3A and 3B shows a different embodiment of the present invention, wherein the portions identical or similar to those shown in FIGS. 1A and 1B are referenced by the same reference numerals. The point of difference of this embodiment from the embodiment shown in FIGS. 1A and 1B lies in that the deodorizing filter 12 is mounted onto the outer surface of the outer side film 8. In other words, the deodorizing filter 12 is mounted on the outer surface of the outer side film 8 of the ostomy bag so as to communicate with the gas discharging vent 11. In this case, the intermediate wall has such a size that, in the state in which the faceplate 1 and the ostomy bag 2 are held vertically, the intermediate wall 13 can horizontally face at least the whole surfaces of the opening 6 in the faceplate 1 and the gas discharging vent 11. In other words, as shown in FIG. 3B, the size of the intermediate wall 13 must be such that broken lines 22 drawn horizontally from the outermost circumference of the opening 6 of the faceplate and broken lines 29 drawn horizontally from the outermost periphery of the gas discharging vent 11 can be accommodated in the surface of the intermediate wall 13.

FIGS. 4A and 4B show still different an embodiment of the present invention, wherein portions identical or similar to those shown in FIGS. 1A and 1B are referenced by the same reference numerals. The point of difference of this embodiment from the embodiment shown in FIGS. 1A and 1B lies in that the lower side 18 of the intermediate wall 13 is partially fixed to the side of the inner side film 7. In this case, the number of partially welding portions 30 in which the lower side 18 of the intermediate wall 13 and the inner side film 7 are spot-welded to each other—(two portions in case of the embodiment shown in FIGS. 4A and 4B) is reduced as compared with that in case of the embodiment shown in FIGS. 1A and 1B. The body wastes discharged from the opening in the faceplate pass through the fluid inlets 31 defined between the welded portions 30 and then smoothly fall toward the bottom of the ostomy bag, wherein it is necessary to ensure that the lower fluid inlets 31 are not blocked up with the body wastes. In the case of this embodiment, the deodorizing filter may likewise be mounted on the outer side of the ostomy bag as in the case of FIGS. 3A and 3B.

Figure 5B:
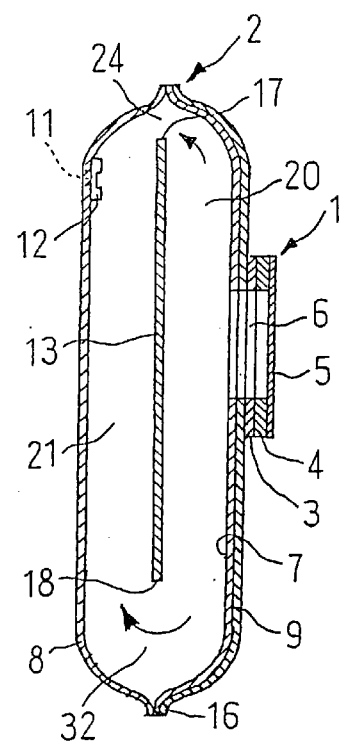
FIG. 5B is a longitudinal sectional view taken along the line B—B in FIG. 5A.

FIGS. 5A and 5B show still different an embodiment of the present invention, wherein portions identical or similar to those shown in FIGS. 1A and 1B are referenced by the same reference numerals. In this embodiment, only sides 14 and 15 of the intermediate wall 13 are fixed to the outer peripheral edges 16 of both films, and the lower side 18 and the upper side 17 are both alike formed as free ends, and, beneath this free end, a fluid inlet 32 is formed. In this case, the body wastes discharged from the opening 6 in the faceplate fall directly to the bottom of the ostomy bag 2. In this embodiment, the deodorizing filter may likewise be mounted on the outer side of the ostomy bag.

Figure 6A:
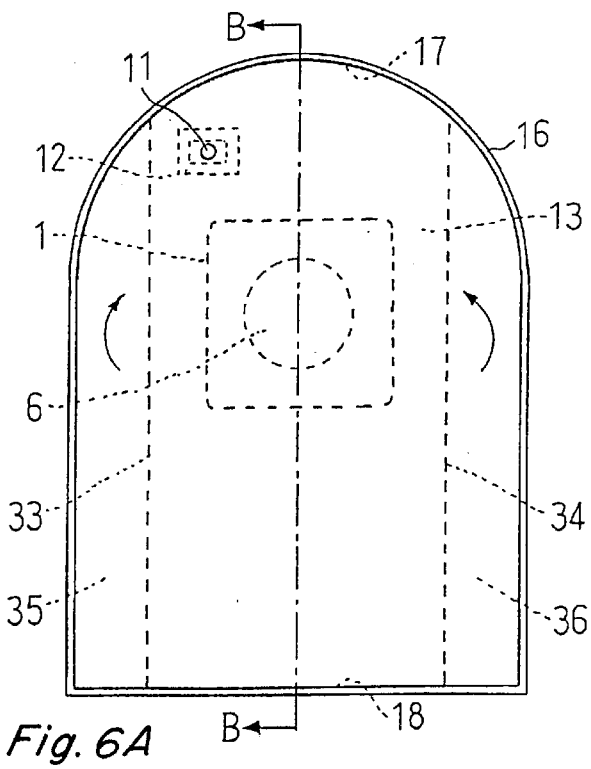
FIG. 6A is a front view of still different an embodiment of the invention.
Figure 6B:
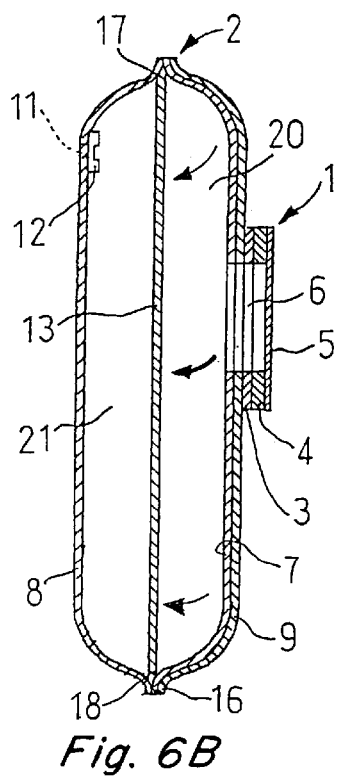
FIG. 6B is a longitudinal sectional view taken along the line B—B in FIG. 6A.

FIGS 6A and 6B show still different an embodiment of the present invention, wherein portions identical or similar to those shown in FIGS. 1A and 1B are referenced by the same reference numerals. In this embodiment, the upper side 17 and the lower side 18 of the intermediate wall 13 are fixed to the outer peripheral edges 16 of both films 7 and 8 of the ostomy bag, the left and right sides 33, 34 of the intermediate wall 13 are free ends so as to form fluid inlets 35 and 36. By providing a plurality of fluid inlets at the right and left sides, fluid inlets can be secured, and the penetration of the body wastes into the deodorizing filter can be prevented. In this embodiment, the deodorizing filter may likewise be mounted on the outer side of the ostomy bag as in the case of FIGS. 3A and 3B.

The respective embodiments described above are all alike of the so-called one-piece ostomy system, but it is apparent that the present invention can be also applied to the so-called two-piece ostomy system in which the faceplate and the ostomy bag can be separated from each other. Further, as for the ostomy bag, in the foregoing embodiments, the ostomy bags that are all closed at the lower ends thereof, but the invention can also be applied to a body waste collector of the type constituted such that the lower end of the ostomy bag is open but closed by a suitable means when in use. The fluid inlets can be formed by the method according to which the fluid inlets are formed between the free end or ends of the intermediate wall and the films of the ostomy bag, the method according to which the fluid inlets are formed by partially fixing the peripheral portion of the intermediate wall to the films of the ostomy bag, or the method according to which the above-mentioned two methods are combined.

Figure 7A:
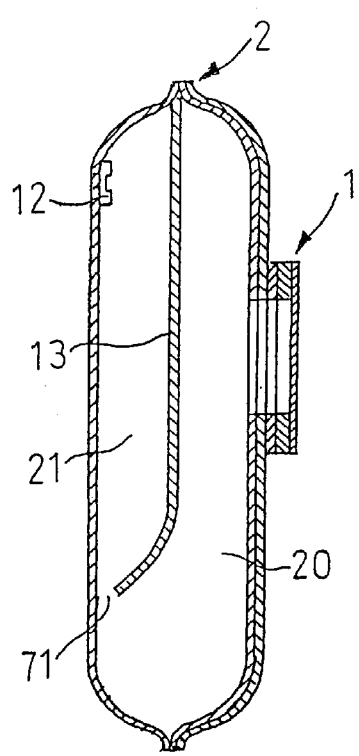
FIGS. 7A and 7B show longitudinal sectional views of different comparative examples with respect to the present invention.
Figure 7B:
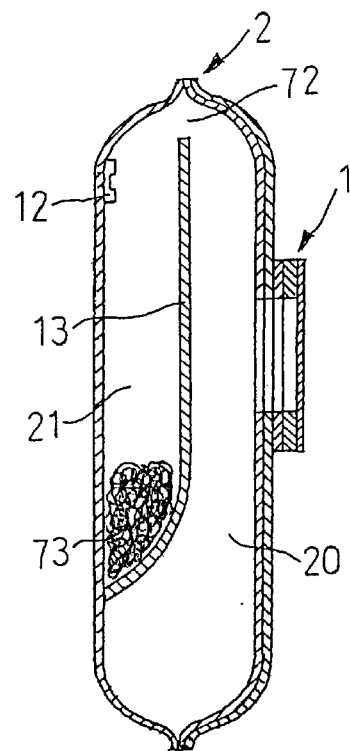

FIGS. 7A and 7B show, for comparison with the present invention in respect of the function, longitudinal sectional views of examples of the body waste collector each constituted such that an intermediate wall is provided, but there is formed only one fluid inlet leading from the region at the faceplate side to the region at the deodorizing filter side, wherein portions identical or similar to those shown in FIGS. 1A and 1B are referenced by the same reference numerals. FIG. 7A shows an example of the body waste collector constituted such that no fluid inlet is provided above the intermediate wall, but only beneath the intermediate wall, a fluid inlet 71 is provided, while FIG. 7B shows an example of the body waste collector constituted such that, only above the intermediate wall, a fluid inlet 72 is provided, but no fluid inlet is provided beneath the intermediate wall. The present inventors requested thirty persons, who had a stoma formed, to put on body waste collectors according to the embodiment shown in FIGS. 1A and 1B and the body waste collectors according to the comparative example shown in FIG. 7A in the same manner as they usually wore their own body waste collectors in order to make a sensuous test for evaluating the degree of gas venting by the three steps, "Good", "Bad" and "Cannot decide either way". The result of this test reveals that, in case of the comparative example, the answers of "Good" amounted to 30%, the answers of "Bad" amounted to 70%, and the answers of "Cannot decide either way" was 0%, whereas, in case of the embodiment of the present invention, the answers of "Good" amounted to 90%, the answers of "Bad" amounted to 10%, and the answers of "Cannot decide either way" was 0%. Thus, through their actual use of the body waste collectors, a very good result was obtained in favor of the present invention. This is because, in case of the comparative example, the body wastes penetrated into the lower fluid inlet and, once the fluid inlet was closed, the body wastes sticking to the fluid inlet were not easily removed to aggravate the discharge of the gases, whereas, in case of the embodiment of the present invention, even if the blockade of the lower fluid inlet is caused as in the case of the comparative example, there was sufficiently achieved the effect that the gases in the ostomy bag could reach the deodorizing filter through the upper fluid inlet and further, there was also produced the effect that the flow-in of the gases from the upper fluid inlet removes the body wastes blocking up the lower fluid inlet; and thus, an obstacle to the discharge of the gases to the outside was hard to be caused. Further, in case of the body waste collector that has a fluid inlet only above the intermediate wall as shown in FIG. 7B, there arises the inconvenience that a part 73 of the body wastes discharged from the opening in the faceplate is accumulated in a region different from the region in which the body wastes are supposed to be collected. From these results, it is understood that, by the provision of fluid inlets in the upper and lower portions of the intermediate wall, the gas venting is markedly improved.

By the present invention, various effects can be achieved as follows:

(1) Since the intermediate wall covers the whole surfaces facing the opening of the faceplate and the deodorizing filter or the gas discharging vent, the deodorizing filter can be prevented from being soiled with the body wastes.

(2) Since there are provided a plurality of fluid inlets leading from the region at the faceplate side to the region at the deodorizing filter or the gas discharging vent side, desirable gas inlets through the ostomy bag at the time of gas venting can be secured, and the gas venting is facilitated; and, even in case the body wastes attach to the fluid inlets between both regions, the body wastes thus sticking to the fluid inlets can be removed by the gas pressure at the time of gas venting; and thus, a good gas venting can be maintained.

(3) In case fluid inlets leading from the region at the faceplate side to the region at the deodorizing filter or the gas discharging vent side are provided above and below the intermediate wall, the body wastes become easy to fall to the lower portion of the ostomy bag at the time of gas venting, and thus, these fluid inlets become hard to be clogged up with the body wastes.

(4) The body waste collector according to the present invention is of a simple constitution in which merely an intermediate wall is additionally provided with the conventional body waste collectors, and any complicated mechanism need not be provided in the deodorizing filter, so that the body waste collector according to the present invention is highly economical as well as advantageous in respect of the manufacture thereof.

What is claimed is:

1. An ostomy bag for receiving body waste discharged from a stoma formed in a human body, said ostomy bag being of the type comprising a first film disposed parallel to, and peripherally sealed to, a second film, so as to define both an inside space between the films and an outside atmosphere; a faceplate coupled to said second film and disposed to allow the ostomy bag to set directly on the stoma; a gas-discharging vent disposed on said first film so as to connect the inside space to the outside atmosphere; and a deodorizing filter exposed to the outside atmosphere but disposed through said first film so as to communicate with the gas-discharging vent; the invention being characterized by, an intermediate wall consisting of a fluid-impermeable material disposed in the inside space, so as to define a first region, extending from said intermediate wall in the direction toward the deodorizing filter, and a second region, extending from said intermediate wall and toward the direction of the faceplate, said intermediate wall being disposed in such a manner as to be substantially parallel to the first and second films, and, the intermediate wall having a peripheral portion partially coupled to the periphery of one or both of the films forming a plurality of fluid inlet openings connecting the first region to the second region adjacent to the periphery of the ostomy bag.

2. The ostomy bag according to claim 1, wherein fluid inlets which connect the first region to the second region are provided in an upper portion and a lower portion of the intermediate wall.

3. The ostomy bag according to claim 2, wherein the lower portion of the intermediate wall is that portion which is partially coupled to the first film of the ostomy bag, while the upper portion is connected to the gas-discharging vent.

4. The ostomy bag according to claim 2, wherein only the sides of the intermediate wall are fixed to the outer peripheral edge of the ostomy bag, and there are formed fluid inlets which connect the first region.

5. The ostomy bag according to claim 1, wherein fluid inlets which connect the first region to the second region are provided outside both sides of the intermediate wall.

6. The ostomy bag according to claim 5, wherein the upper portion and the lower portion of the intermediate wall are fixed to an outer peripheral edge of the ostomy bag, and fluid inlets which connect the first region to the second region via lateral sides of the intermediate wall.

7. The ostomy bag according to any of claims 1 to 6, wherein the deodorizing filter has a thickness of at least 1 mm.

8. The ostomy bag according to claim 1, wherein grooves are in the deodorizing filter and lie next to the first film.

9. The ostomy bag according to claim 1, wherein the deodorizing filter, at a point near the intermediate wall, is rugged.

* * * * *